US010299474B2

(12) United States Patent
Su et al.

(10) Patent No.: US 10,299,474 B2
(45) Date of Patent: May 28, 2019

(54) COMPOSITIONS CONTAINING ANTHRAQUINONE DERIVATIVES AS GROWTH PROMOTERS AND ANTIFUNGAL AGENTS

(71) Applicant: Marrone Bio Innovations, Inc., Davis, CA (US)

(72) Inventors: Hai Su, Woodland, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 522 days.

(21) Appl. No.: 14/148,566

(22) Filed: Jan. 6, 2014

(65) Prior Publication Data

US 2014/0116307 A1   May 1, 2014

Related U.S. Application Data

(62) Division of application No. 13/288,864, filed on Nov. 3, 2011, now Pat. No. 8,658,567.

(60) Provisional application No. 61/410,279, filed on Nov. 4, 2010.

(51) Int. Cl.
| | | |
|---|---|---|
| A01N 35/06 | (2006.01) |
| A01N 65/00 | (2009.01) |
| A01N 65/30 | (2009.01) |
| A01C 1/06 | (2006.01) |
| A01C 7/00 | (2006.01) |
| A01N 25/00 | (2006.01) |

(52) U.S. Cl.
CPC ............. *A01N 35/06* (2013.01); *A01C 1/06* (2013.01); *A01C 7/00* (2013.01); *A01N 25/00* (2013.01); *A01N 65/00* (2013.01); *A01N 65/30* (2013.01)

(58) Field of Classification Search
CPC ........ A01N 35/06; A01N 65/00; A01N 65/30; A01N 25/00; A01C 1/06; A01C 7/00
See application file for complete search history.

(56) References Cited

U.S. PATENT DOCUMENTS

| | | | |
|---|---|---|---|
| 2,339,335 A * | 1/1944 | Heckmanns | .......... C07C 49/747 504/284 |
| 3,726,850 A | 4/1973 | Detroit et al. | |
| 3,813,236 A | 5/1974 | Allan et al. | |
| 3,929,453 A | 12/1975 | Dimitri et al. | |
| 4,381,194 A | 4/1983 | DelliColli et al. | |
| 4,602,004 A | 7/1986 | Cohen | |
| 4,612,051 A | 9/1986 | Miller et al. | |
| 4,666,522 A | 5/1987 | Hollis et al. | |
| 4,863,734 A | 9/1989 | Pommer et al. | |
| 4,975,459 A | 12/1990 | Mehta et al. | |
| 5,300,521 A | 4/1994 | Eberle et al. | |
| 5,668,183 A | 9/1997 | Leuenberger | |
| 5,885,604 A | 3/1999 | Ballinger | |
| 5,989,429 A | 11/1999 | Bardinelli et al. | |
| 5,994,266 A | 11/1999 | Hobbs et al. | |
| 6,172,004 B1 | 1/2001 | Brinker et al. | |
| 7,344,730 B1 | 3/2008 | Stadler et al. | |
| 7,867,507 B2 | 1/2011 | Birthisel et al. | |
| 2003/0012804 A1 | 1/2003 | Cutler et al. | |
| 2004/0096428 A1 | 5/2004 | Jijakli et al. | |
| 2005/0163815 A1 | 7/2005 | Bowen et al. | |
| 2006/0247130 A1 | 11/2006 | Van der Krieken et al. | |
| 2007/0148401 A1 | 6/2007 | McGlade et al. | |
| 2007/0149401 A1* | 6/2007 | Haskell | .................. A01N 37/42 504/103 |
| 2007/0191292 A1 | 8/2007 | Gandhi et al. | |
| 2007/0264363 A1 | 11/2007 | Bowen et al. | |
| 2008/0113920 A1 | 5/2008 | Yang et al. | |
| 2008/0193387 A1 | 8/2008 | De Wolff et al. | |
| 2009/0246293 A1 | 10/2009 | Ehr et al. | |
| 2010/0136132 A1 | 6/2010 | Van der Krieken et al. | |
| 2010/0154498 A1 | 6/2010 | Valencia | |
| 2010/0278890 A1 | 11/2010 | Winowiski | |
| 2011/0015237 A1 | 1/2011 | Morita et al. | |
| 2011/0028500 A1 | 2/2011 | Su et al. | |
| 2011/0082215 A1 | 4/2011 | Huang et al. | |
| 2012/0196751 A1 | 8/2012 | Namnath et al. | |

FOREIGN PATENT DOCUMENTS

| | | |
|---|---|---|
| CN | 1063597 A | 8/1992 |
| CN | 1387765 A | 1/2003 |
| CN | 1515152 A | 7/2004 |
| DE | 4411895 | 5/1995 |
| EP | 0173410 | 3/1986 |
| JP | H62-129209 | 6/1987 |
| JP | 08-099813 A | 4/1996 |
| JP | H0899813 | 4/1996 |
| JP | H0899813 A | 4/1996 |
| JP | H08109112 | 4/1996 |
| JP | H08-333297 A | 12/1996 |

(Continued)

OTHER PUBLICATIONS

Inderjit et al., On the Ollelopathic Potential of Certain Terpenoids, Phenolics, and Their Mixtures, and Their Recovery from Soil, 1997, Canadian Journal of Botany, vol. 75 No. 6, pp. 888-891.*
Zhang et al., Antioxidant Activity of Anthraquinones and Flavonoids from Flower of Reynoutria sachalinensis, 2005, Arch Pharm Res, vol. 28 No. 1, pp. 22-27.*
Inoue et al., Allelochemicals from Polygonum sachalinense Fr. Schm. (Polygonacea), 1992, Journal of Chemical Ecology, vol. 18 No. 10, pp. 1833-1840.*
Su et al., Regalia® Bioprotectant in Plant Disease Management, Feb. 2012, Outlooks on Pest Management, pp. 30-34.*
Agarwal, S. et al., "Antifungal Activity of Anthraquinone Derivatives from *Rheum emodi*," *J. Ethnopharmacol.* 72:43-46 (2000).
Bardin, M. et al., "Compatibility Between Biopesticides Used to Control Grey Mould, Powdery Mildew and Whitefly on Tomato," *Biological Control* 46:476-483 (2008).

(Continued)

*Primary Examiner* — Ali Soroush

(74) *Attorney, Agent, or Firm* — Chainey P. Singleton; Ying-Horng Liu

(57) ABSTRACT

Compositions for modulating plant growth, seed germination and soil borne diseases comprising anthraquinone derivatives are disclosed.

5 Claims, No Drawings

(56) References Cited

FOREIGN PATENT DOCUMENTS

| | | |
|---|---|---|
| JP | 2000-033383 | 2/2000 |
| JP | 2000-034202 | 2/2000 |
| JP | 200164112 A | 3/2001 |
| RU | 2390130 C1 | 5/2010 |
| RU | 2395967 C1 | 8/2010 |
| WO | 94/17070 A1 | 8/1994 |
| WO | WO 9811782 | 3/1998 |
| WO | 02080673 A1 | 10/2002 |
| WO | WO 2003005816 | 1/2003 |
| WO | WO 2004000014 | 12/2003 |
| WO | WO 2005010315 | 2/2005 |
| WO | WO 2006015865 | 2/2006 |
| WO | WO 2006037632 | 4/2006 |
| WO | WO 2006037633 | 4/2006 |
| WO | WO 2006037634 | 4/2006 |
| WO | WO 2010040834 | 4/2010 |

OTHER PUBLICATIONS

Bartlett, D.W. et al., "The Strobilurin Fungicides," *Pest Management Science* 58:649-662 (2002).

Belanger, R.R. et al., "Challenges and Prospects for Integrated Control of Powdery Mildews in the Greenhouse," *Can. J. Plant Pathol.* 19:310-314 (1997).

Bokshi, A.I. et al., "A Single Application of Milsana® Followed by Bion® Assists in the Control of Powdery Mildew in Cucumber and Helps Overcome Yield Losses," *J. Horticltural Science & Biotechnology* 83:701-706 (2008).

Braun, U. et al., "The Taxonomy of the Powdery Mildew Fungi," In *The Powdery Mildews: A Comprehensive Treatise*. R.R. Belanger et al. eds. APS Press, St. Paul, MN, pp. 13-55 (2002).

BRAVO Fungicide draft, 10-1000L Draft Label Text. Container (Apr. 2009).

Burpee, L. et al., "Reassessment of Fungicide Synergism for Control of Dollar Spot," *Plant Disease* 92:601-606 (2008).

Captan, General Fact Sheet. National Pesticide Information Center (2002).

Daayf, F. et al., "The Effects of Plant Extracts of *Reynoutria sachalinensis* on Powdery Mildew Development and Leaf Physiology of Long English Cucumber," *Plant Disease* 79:577-580 (1995).

De Waard, M.A., "Synergism and Antagonism in Fungicide Mixtures Containing Sterol Demethylation Inhibitors," *Phytopathology* 86:1280-1283 (1996).

Dow AgroSciences Nova™ 40W Agricultural Fungicide, Material Safety Data Sheet (Mar. 2009).

Durrant, W.E. et al., "Systemic Acquired Resistance," *Annu. Rev. Phytopathol.* 42:185-209 (2004).

Fofana, B. et al., "Milsana-Induced Resistance in Powdery Mildew-Infected Cucumber Plants Correlates With the Induction of Chalcone Synthase and Chalcone Isomerase," *Physiol. Molec. Plant Pathol.* 61:121-132 (2002).

Fongicide ELEVATE® 50 WDG, Arysta LifeScience North America LLC, (Aug. 2007) (French language document).

Fraaije, B.A. et al., "QoI Resistance Development in Populations of Cereal Pathogens in the UK," *Crop Science & Technology* pp. 689-694 (2003).

Gisi, U., "Synergistic Interaction of Fungicides in Mixtures," *Phytopathology* 86:1273-1279 (1996).

Hafez, M.B. et al., "The Side-Effects of Plant Extracts and Metabolites of *Reynoutria sachalinensis* (F. Schmidt) Nakai and Conventional Fungicides on the Beneficial Organism *Trichogramma cacoeciae* Marchal (Hym., Trichogrammatidae)," *J. Appl. Ent.* 123:363-368 (1999).

Holb, I.J. et al., "The Benefits of Combining Elemental Sulfur with a DMI Fungicide to Control *Monilinia fructicola* Isolates Resistant to Propiconazole," *Pest Management Science* 64:156-164 (2008).

Horst, R.K. et al., "Effect of Sodium Bicarbonate and Oils on the Control of Powdery Mildew and Black Spot of Roses," *Plant Disease* 76:247-251 (1992).

Hwang, S-F. et al., "Effect of Seed Treatments and Root Pathogens on Seedling Establishment and Yield of Alfalfa, Birdsfoot Trefoil and Sweetclover," *Plant Pathology Journal* 5:322-328 (2006).

Inoue, M. et al., "Allelochemicals From *Polygonum sachalinense* Fr. Schm. (Polygonaceae)," *Journal of Chemical Ecology* 18:1833-1840 (1992).

Izhaki, I., "Emodin—A Secondary Metabolite with Multiple Ecological Functions in Higher Plants," *New Phytologist* 155:205-217 (2002).

James, C., "A Manual of Assessment Keys for Plant Diseases," Canada Department of Agriculture Publication No. 1458 1971, Key Nos. 2.2 and 2.4. American Phytopathological Society, St. Paul, MN. (1971).

Karaoglanidis, G.S. et al., "Efficacy of Strobilurins and Mixtures with DMI Fungicides in Controlling Powdery Mildew in Field-Grown Sugar Beet," *Crop Protection* 25:977-983 (2006).

Keinath, A.P., et al., "Use of Biofungicides and Reduced-Risk Fungicides Rotated With Chlorothalonil to Control Downy Mildew on Muskmelon, 2002," *F&N Tests Report* No. 58:V024 (2002).

Keinath, A.P. et al., "Reduced-Risk Fungicides Rotated or Mixed with Chlorothalonil to Manage Downy Mildew on Muskmelon, 2003," *F&N Tests Report* No. 59:V004 (2003).

Kim, Y-M. et al., "Anthraquinones Isolated from *Cassia tore* (Leguminosae) Seed Show an Antifungal Property Against Phytopathogenic Fungi," *J. Agric. Food Chem.* 52:6096-6100 (2004).

Kong, L.D., et al., "Inhibition of MAO A and B by Some Plant-Derived Alkaloids, Phenols and Anthraquinones," *J. Ethnopharmacology* 91:351-355 (2004).

Konstantinidou-Doltsinis, S. et al., "Control of Powdery Mildew of Grape in Greece Using Sporodex® L and Milsana®," *J. Plant Dis. Protect.* 114:256-262 (2007).

Krishnakumari, G.N., et al., "Antifeedant Activity of Quinones from *Ventilago Madaraspatana*," *Fitoterapia* 72:671-675 (2001).

Kuc, J., "Development and Future Direction of Induced Systemic Resistance in Plants," *Crop Protection* 19:859-861 (2000).

Langston, D.B., et al., "Control of Alternaria Leaf Spot of Muskmelon with Biofungicides and Reduced-Risk Fungicides Alternated with Chrlothalonil, 2002," *F&N Tests Report* No. 58:V082 (2002).

Langston, D.B., "Rotation of Biocides with Powdery Mildew Fungicides to Suppress Powdery Mildew of Squash in Georgia, 2003," *F&N Tests Report* No. 59:V135 (2003).

Langston, D.B., "Evaluation of Fungicides and Spray Programs for Control of Powdery Mildew in Summer Squash in Georgia II, 2004," *F&N Tests Report* No. 60:V137 (2004).

Lehnhof, F., "Milsana® A *Reynoutria sachalinensis* Based Plant Extract for Preventive Control of Powdery Mildew," BIOFA; http://www.abim.ch/fileadmin/documents-abim/presentations2007/session5/1_lehnhof_abim_2007.pdf (2007).

Limpel, L.E. et al., "Weed Control by Dimethyl Tetrachloroterephthalate Alone and in Certain Combinations," *N.E. Weed Control Conference* 16:48-53 (1962).

Liu, S.Y., et al., "Anthraquinones in *Rheum palmatum* and *Rumex dentatus* (Polygonaceae), and Phorbol Esteres in *Jatropha curcas* (Euphorbiaceae) with Molluscicidal Activity Against the Schistosome Vector Snails *Oncomelania, Biomphalaria* and *Bulinus*," *Tropical Medicine and International Health*, 2:179-188 (1997).

Matheron, M.E., et al., "Evaluation of Fungicides for Management of Powdery Mildew on Lettuce, 2003," *F&N Tests Report* No. 59:V089 (2003).

May, R.M., "Evolution of Pesticide Resistance," *Nature* 315:12-13 (1985).

Mcgrath, M.T., et al., "Evaluation of Fungicide Programs for Managing Powdery Mildew of Pumpkin, 2000," *F&N Tests Report* No. 56:V76 (2000).

Mcgrath, M.T., "Evaluation of Fungicide Programs for Managing Powdery Mildew of Pumpkin, 2001," *F&N Tests Report* No. 57:V086 (2001).

Mcgrath, M.T., "Fungicide Resistance in Cucurbit Powdery Mildew: Experiences and Challenges," *Plant Disease* 85:236-245 (2001).

(56) References Cited

OTHER PUBLICATIONS

Mcgrath, M.T., "Occurrence of Strobilurin Resistance and Impact on Managing Powdery Mildew of Cucurbits," *Cornell University Vegetable MD Online* (2003).
Mcgrath, M.T., "Guidelines for Managing Cucurbit Powdery Mildew in 2006," *Cornell University Vegetable MD Online* (2006).
Muravieva, D.A., "Pharmacognosy," Medicine Publishing House, Moscow, pp. 494-529 (1978).
Nash, R.G., "Phytotoxic Interaction Studies—Techniques for Evaluation and Presentation of Results," *Weed Science* 29:147-155 (1981).
PENNCOZEB® 80 WP fungicide. Group M Fungicide—label and booklet (2008) (Pest Management Regulatory Agency label transcript service).
Pesticide Alert, Strawberry News Bulletin—Cabrio Registered for Use on Strawberries (Feb. 24, 2003) (English and Spanish).
Randoux, B., et al., "Inhibition of *Blumeria graminis* f. sp. *tritici* Germination and Partial Enhancement of Wheat Defenses by Milsana," *Phytopathology* 96:1278-1286 (2006).
REGALIA® Bioprotectant Concentrate Label (May 2009).
REGALIA® SC A Powerful New Tool for Powdery Mildew and Gummy Stem Blight on Cucurbits Fact Sheet 1 (May 2009).
REGALIA® SC A Powerful New Tool for Powdery Mildew Control on Cucurbits Fact Sheet 2 (May 2009).
Reuveni, M., "Improved Control of Powdery Mildew (*Sphaerotheca pannosa*) of Nectarines in Israel Using Strobilurin and Polyoxin B Fungicides; Mixtures with Sulfur; and Early Bloom Applications," *Crop Protection* 20:663-668 (2001).
Richer, D.L., "Synergism—a Patent View," *Pesticide Science*19:309-315 (1987).
Rosenberger, D.A., et al., "Controlling Diseases on Jerseymac and Ginger Gold Apples with Biocontrol and Contact Fungicides, 1999," *F&N Tests Report* No. 55:25 (1999).
Ross, A.F., "Systemic Acquired Resistance Induced by Localized Virus Infections in Plants," *Virology* 14:340-358 (1961).
Samoucha, Y. et al., "Synergy Between Metalaxyl and Mancozeb in Controlling Downy Mildew in Cucumbers," *Phytopathology* 74:1434-1437 (1984).
Schilder, A.M.C., et al., "Evaluation of Fungicides for Control of Foliar Diseases of Strawberries, 2003," *F&N Tests Report* No. 59:SMF029 (2003).
Schmitt, A., "Induced Responses by Plant Extracts From Reynoutria sachalinensis: A Case Study," *Induced Resistance in Plants against Insects and Diseases IOBC/wprs Bull.* 25:83-88 (2002).
Schmitt, A., "Biocontrol of Plant Pathogens with Microbial BCAs and Plant Extracts-Advantages of Single and Combined Use," *Modern Fungicides and Antifungal Compounds IV: Proceedings of the 14th International Reinhardsbrunn Symposium 2004*, Alton, UK pp. 205-225 (2005) (Abstract only).
Schmitt, A. et al., "Use of *Reynoutria sachalinensis* Plant Extracts, Clay Preparations and Brevibacillus brevis Against Fungal Diseases of Grape Berries," *10th International Conference on Cultivation Technique and Phytopathological Problems in Organic Fruit-Growing and Viticulture*, Weinsberg, Germany7, pp. 146-151 (2002).
Schnabel, G. et al., "Reduced Sensitivity in *Monilinia fructicola* to Propiconazole in Georgia and Implications for Disease Management," *Plant Dis.* 88:1000-1004 (2004).
Singh, D.N., et al., "Antifungal Anthraquinones from *Saprosma fragrans*," *Bioorganic & Medicinal Chemistry Letters* 16:4512-4514 (2006).
Stromberg, E.L., "Evaluation of Foliar Fungicides and a Botanical for Disease Control in FFR 555 Soft Red Winter Wheat in Virginia, 1999," *F&N Tests Report* No. 55:353 (1999).
Su, H. et al., "Sporulation of *Bremia lactucae* Affected by Temperature, Relative Humidity, and Wind in Controlled Conditions," *Phytopathology* 94:396-401 (2004).
Tamokou, J.D.D., et al., "Antimicrobial Activities of Methanol Extract and Compounds From Stem Bark of *Vismia rubescens*," *J. Ethnopharmacology*, 124:571-575 (2009).

Tiebre, M-S., et al., "Hybridization and Sexual Reproduction in the Invasive Alien *Fallopia* (Polygonaceae) Complex in Belgium," *Annals of Botany*, 99:193-203 (2007).
Van Den Bosch, F. et al., "Models of Fungicide Resistance Dynamics," *Annu. Rev. Phytopathol.* 46:123-147 (2008).
Van Loon, L.C. et al., "Systemic Resistance Induced by Rhizosphere Bacteria," *Annu. Rev. Phytopathol.* 36:453-483 (1998).
Vechet, L. et al., "A Comparative Study of the Efficacy of Several Sources of Induced Resistance to Powdery Mildew (*Blumeria graminis* f. sp. *tritici*) in Wheat Under Field Conditions," *Crop Protection* 28:151-154 (2009).
Verma, S.C., et al., "Determination and Locational Variations in the Quantity of Hydroxyanthraquinones and Their Glycosides in Rhizomes of *Rheum emodi* Using High-Performance Liquid Chromatography," *J. Chromatography A* 1097:59-65 (2005).
Vrchotova, N., et al., "The Stilbene and Catechin Content of the Spring Sprouts of *Reynoutria* Species," *Acta Chromatographica* 19:21-28 (2007).
Walters, D. et al., "Induced Resistance for Plant Disease Control: Maximizing the Efficacy of Resistance Elicitors," *Phytopathology* 95:1368-1373 (2005).
Werner, S.J., et al., "Anthraquinone-Based Bird Repellent for Sunflower Crops," *Applied Animal Behaviour Science*, 129:162-169 (2011).
Wurms, K. et al., "Effects of Milsana and Benzothiadiazole on the Ultrastructure of Powdery Mildew Haustoria on Cucumber," *Phytopathology* 89:728-736 (1999).
Wyenandt, C.A. et al., "Fungicide Resistance Management Guidelines for Cucurbit Downy and Powdery Mildew Control in the Mid-Atlantic and Northeast Regions of the U.S.," *Phytopathology* 99:S144 (2009).
Yang, X, et al., "Synergistic Interaction of Physcion and Chrysophanol on Plant Powdery Mildew," *Pest Management Science* 63:511-515 (2007).
Examination Report in New Zealand Patent App. No. 598365, dated Sep. 17, 2012.
Examination Report in New Zealand Patent App. No. 599664, dated Nov. 29, 2012.
Final Office Action in U.S. Appl. No. 12/845,883, dated Oct. 18, 2012.
International Preliminary Report on Patentability in PCT App. No. PCT/US2010/043612, dated Feb. 9, 2012.
International Preliminary Report on Patentability in PCT App. No. PCT/US2010/051359, dated Apr. 19, 2012.
International Search Report and Written Opinion in PCT App. No. PCT/US2010/051359, dated Jun. 24, 2011.
International Search Report and Written Opinion in PCT App. No. PCT/US2010/043612, dated Aug. 2, 2011.
International Search Report and Written Opinion in PCT App. No. PCT/US2010/043612, dated Jul. 29, 2010.
International Search Report in PCT App. No. PCT/US12/23571, dated May 24, 2012.
International Search Report in PCT App. No. PCT/US2011/059197, dated Jun. 29, 2012.
International Search Report and Invitation to Pay Fees for Additional Search in PCT App. No. PCT/US2010/043612, dated May 2, 2011.
Office Action in U.S. Appl. No. 12/845,883, dated Mar. 15, 2012.
Office Action in U.S. Appl. No. 12/897,776, dated Aug. 2, 2012.
"*Rheum palmatum* and *Rheum rhabarbarum*," retrieved from the internet: http://www.ansci.cornell.edu/plants/medicinal/rhub.html (Internet archive date: May 19, 2000; accessed Mar. 9, 2012).
Supplementary European Search Report in EP App. No. 10805012.1 dated Dec. 13, 2013, 11 pages.
Nishimura, Hiroyuki et al. "Identification of Allelochemicals in Eucalyptus citriodora and Polygonum sachalinense" American Cancer Society (1995) pp. 74-85.
Inoue, M. et al., "Allelochemicals From Polygonum sachalinense Fr. Schm. (Polygonaceae)" Journal of Chemical Ecology, vol. 18, No. 10, 1992.
Office Action CN201510171217.3 dated Apr. 28, 2016 [Machine Translation—English].

(56) References Cited

OTHER PUBLICATIONS

Choi, Ja. Gyung., et al., "Effects of chrysophanol, parietin, and nepodin of Rumex crispus on barley and cucumber powdery mildews." Crop Protection, May 7, 2004, vol. 23, pp. 1215-1221.
Kim, Mi-Young., et a., "Anthraquinones Isolated from Cassia tora (*Leguminosae*) Seed Show an Antifungal Property against Phytopathogenic Fungi." Journal of Agricultural and Food Chemistry, Sep. 4, 2004, vol. 52, No. 20, pp. 6096-6100.
Konstantinidou-Doltsinis, S., et al., "Efficacy of Milsana a formulated plant extract from Reynoutria sachalinensis, against powdery mildew of tomato (*Leveillula taurica*)." BioControl, Jun. 2006, vol. 51, No. 3, pp. 375-392.
Database EMBL Accession No. XP-002728307 Dated Sep. 30, 1994.
Database EMBL Accession No. XP-002728308 Dated Jun. 5, 1995.
F. Vinale et al., "A Novel Role for Trichoderma Secondary Metabolites in the Interactions with Plants," Physiological and Molecular Plant Pathology Journal 72, May 28, 2008, pp. 80-86.
Inderjit et al., "Effect of the Anthraquinones Emotion and Physician on Availability of Selected Soil Inorganic Ions," Association of Applied Biologists, 1999, 135, pp. 425-429.
Costa Rica Office Action dated May 22, 2018, and Reporting Letter dated Jun. 6, 2018.
India Examination Report dated Jun. 14, 2018, pp. 1-6.

\* cited by examiner

COMPOSITIONS CONTAINING ANTHRAQUINONE DERIVATIVES AS GROWTH PROMOTERS AND ANTIFUNGAL AGENTS

RELATED APPLICATIONS

This application is a divisional application of U.S. application Ser. No. 13/288,864, filed Nov. 3, 2011, which claims the benefit under 35 U.S.C. § 119(e) to U.S. Provisional Application No. 61/410,279, filed Nov. 4, 2010, both of which are hereby incorporated by reference.

TECHNICAL FIELD

Disclosed herein are uses of compositions, particularly, plant extracts containing anthraquinone derivatives for modulating growth of plants, modulating establishment of roots in the plants and modulating germination of seeds in plants. Also disclosed are uses of plant extracts containing anthraquinone derivatives for modulating, in particular, controlling soil-borne diseases in plants.

BACKGROUND

Extract from giant knotweed (*Reynoutria sachalinensis*) sold as MILSANA® and REGALIA® by Marrone Bio Innovations, Inc. provides control of powdery mildew and other plant diseases on cucurbits and other crops mainly by inducing an accumulation of fungitoxic phenolic compounds in the plant (Daayf et al., 1995; Wurms et al. 1999; Schmitt, 2002). Recently, formulated giant knotweed extract has also shown great efficiency in inducing resistance in various crops against plant pathogens including wheat powdery mildew (Vechet et al., 2009). Besides the induced systemic resistance (ISR) mode of action, the formulated *R. sachalinensis* extract has recently also been shown to have a direct fungistatic effect against wheat powdery mildew (*Blumeria graminis* f. sp. *tritici*; Randoux et al., 2008).

Plant defense inducers such as the extract of *Reynoutria sachalinensis* have been tested in tank mixes and rotations with other SAR/ISR products as well as with biocontrol agents (BCA) (Hafez et al., 1999; Belanger and Benyagoub, 1997; Schmitt et al. 2002; Schmitt and Seddon, 2005; Bardin et al., 2008). The purpose of these studies has mainly been to demonstrate the compatibility of different types of plant extracts with biocontrol agents. Konstatinidou-Doltsinis et al. (2007) tested the *R. sachalinensis* product in a rotation with *Pseudozyma flocculosa* product against powdery mildew on grapes, and found that alternated application of both products improved the efficacy of *R. sachalinensis*. In the same study, alternation of sulfur and *R. sachalinensis* in a rotation did not have a beneficial effect. Belanger and Benyagoub (1997) found that the yeast-like fungus, *Pseudozyma flocculosa*, was compatible with *Reynoutria sachalinensis* when used against cucumber powdery mildew in a greenhouse. Similarly, Bokshi et al. (2008) evaluated the combined effect of an acquired systemic resistance activator benzothiadiazole and MILSANA® against cucumber powdery mildew, and found that MILSANA® used in a rotation with benzothiadiazole provided an effective control measure against powdery mildew in the field. However, based on the disease severity and yield data collected, it was not possible to determine whether the positive effect was additive or synergistic.

SUMMARY

Provided herein is a use of a composition containing one or more anthraquinone derivatives that modulate and in particular, promote plant growth in a plant (e.g. crops such as fruit (e.g., strawberry), vegetable (e.g., tomato, squash, pepper, eggplant), or grain crops (e.g., soy, wheat, rice, corn) tree, flower, ornamental plant, shrub (e.g., cotton, rose), bulb plant (e.g, onion, garlic) or vine (e.g., grape vine) and also, in particular, modulate or promote root establishment. In a related aspect, provided is a method for modulating growth in a plant (e.g. crops such as fruit (e.g., strawberry), vegetable (e.g., tomato, squash, pepper, eggplant), or grain crops (e.g., soy, wheat, rice, corn), tree, flower, ornamental plant, shrub (e.g., cotton, rose), bulb plant (e.g, onion, garlic) or vine (e.g., grape vine) with an amount of a composition containing one or more anthraquinone derivatives which modulate and in particular promote growth by, for example, modulating or in particular, promoting root establishment in said plant.

In a particular embodiment, the composition may be a plant extract or, in other words, an extract derived from a plant. The extract may be derived from the family Polygonacae (e.g., *Reynoutria sachalinensis*).

The extract may be applied to the roots of a plant before transplanting it to soil. Thus provided is a method for modulating root extension in a plant comprising: (a) treating one or more roots of a plant with said extract in an amount effective to modulate root extension when transplanted into soil; (b) transplanting the treated plant of (a) into soil.

In a related aspect, also provided is a composition for use in modulating growth in a plant comprising one or more anthraquinone derivatives which modulate growth in a plant and optionally a second substance, wherein said second substance is a plant growth promoting agent.

Also provided is a use of a composition, which may be an extract containing or comprising one or more anthraquinone derivatives that modulate germination of a seed in a plant e.g. crops such as fruit (e.g., strawberry), vegetable (e.g., tomato, squash, pepper, eggplant), or grain crops (e.g., soy, wheat, rice, corn), tree, flower, ornamental plant, shrub (e.g., cotton, rose), bulb plant (e.g., onion, garlic) or vine (e.g., grape vine) for modulating such germination. In a related aspect, provided is a method for modulating germination of a seed in a plant by treating said plant with an amount of a composition containing one or more anthraquinone derivatives that modulate soil-borne disease infection in a plant effective to modulate said germination of a seed in a plant. Again the composition may be a plant extract.

In a related aspect, also provided, is a composition for use in modulating germination of a seed in a plant comprising one or more anthraquinone derivatives which modulate germination of a seed in a plant and optionally a second substance, wherein said second substance is a seed coating agent.

Also provided is a use of a composition, which may be an extract containing or comprising one or more anthraquinone derivatives that modulate and in particular, modulate soil-borne diseases, in particular, non-*Rhizoctonia* soil borne diseases in a plant (e.g. crops such as fruit (e.g., strawberry), vegetable (e.g., tomato, squash, pepper, eggplant), or grain crops (e.g., soy, wheat, rice, corn), tree, flower, ornamental plant, shrub (e.g., cotton, rose), bulb plant (e.g, onion, garlic) or vine (e.g., grape vine). In a related aspect, provided is a method for modulating soil-borne disease infection in a plant by treating said plant with an amount of a composition containing one or more anthraquinone derivatives that modulate soil-borne disease infection in a plant effective to modulate said soil-borne disease infection in a plant. Again, the composition may be a plant extract.

In a related aspect, also provided is a composition for use in modulating soil borne disease in a plant comprising one or more anthraquinone derivatives which modulate soil borne disease in a plant and optionally a second substance, wherein said second substance is a plant anti-phytopathogenic agent.

In the compositions and methods set forth above, the plant may be a fruit, vegetable, tree, shrub, bulb plant, vine. The fruit, vegetable, tree, flower, ornamental plant, shrub, bulb plant, vine may include but are not limited to strawberry, squash, cucumber, tomato, roses, pepper, cotton, eggplant, onion and garlic, soy, wheat, rice, corn, grapevines.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise. For example, "a fungus" also encompasses "fungi".

As defined herein, the term "modulate" is used to mean to alter the amount of growth and preferably increase the amount or rate of growth or germination of a seed of a plant or alter and preferably decrease the amount of soil-borne disease infection present in a fruit or vegetable or rate of spread of a soil-borne disease infection in a plant.

Compositions

The compositions used in the methods set forth in the instant disclosure contain anthraquinone derivatives as biochemical agricultural products for use in modulating and preferably promoting plant growth, and/or modulating and preferably promoting seed germination and/or modulating and preferably inhibiting soil borne plant disease infection. In particular the composition may be a plant extract. Thus, "contain" also encompasses extracts that produce said anthraquinone derivatives. In a particular embodiment, the anthraquinone derivative(s) used is (are) the major active ingredients or one of the major active ingredients.

Anthraquinone derivatives include, but are not limited to, physcion, emodin, chrysophanol, ventiloquinone, emodin glycoside, chrysophanol glycoside, physcion glycoside, 3,4-dihydroxy-1-methoxy anthraquinone-2-corboxaldehyde, damnacanthal. These derivatives share a similar structure as follows:

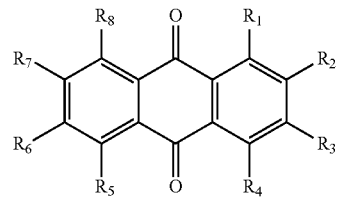

Where $R_1$, $R_2$, $R_3$, $R_4$, $R_5$, $R_6$, $R_7$ and $R_8$ are hydrogen, hydroxyl, hydroxylalkyl, halogen, carboxyl, alkyl, alkyoxyl, alkenyl, alkenyloxyl, alkynyl, alkynyloxyl, heterocyclyl, aromatic, or aryl group, sugars such as glucose.

In a particular embodiment, provided are anthraquinone derivatives that may be contained in or derived from extracts derived from plant families including but not limited to Polygonaceae, Rhamnaceae, Fabaceae, Asphodelaceae, and Rubiaceae so on. In particular, these compounds can be derived from any part of plants such as leaf, stem, bark, root and fruits. Plant materials can be wet and dry, but preferably dry plant materials. As defined herein, "derived from" means directly isolated or obtained from a particular source or alternatively having identifying characteristics of a substance or organism isolated or obtained from a particular source. To meet the biochemical agricultural products, solvents and processes that are used in the extraction and purification must meet the requirements of National Organic Program (NOP) [http://www.ams.usda.gov/AMSv1.0/nop, cited on Jul. 20, 2009].

In a more particular embodiment, the plant extract is derived from a member of the Polygonaceae family. In a particular embodiment, extract in said combination contains the anthraquinone derivatives physcion and optionally emodin. Members of the Polygonaceae family include, but are not limited to, *Acetosella, Antigonon, Aristocapsa, Bilderdykia, Brunnichia, Centrostegia, Chorizanthe, Coccoloba, Coccolobis, Coccolobo, Corculum, Dedeckera, Delopyrum, Dentoceras, Dodecahema, Emex, Eriogonum, Fafopyrum, Fagopyrum, Fallopia, Gilmania, Goodmania, Harfordia, Hollisteria, Koenigia, Lastarriaea, Mucronea, Muehlenbeckia, Nemacaulis, Oxyria, Oxytheca, Perscarioa, Persicaria, Pleuropterus, Podopterus, Polygonella, Polygonum, Pterostegia, Rheum, Rumex, Ruprechtia, Stenogonum, Systenotheca, Thysanella, Tovara, Tracaulon, Triplaris* and even more particular embodiment, the extract may be derived from a *Reynoutria* (alternately referred to as *Fallopia*) sp or *Rheum* species. In a most particular embodiment, the extract is derived from *Reynoutria sachalinensis*.

Plant Growth Promoting Agents

The compositions set forth above which may be in the form of an extract (such as products marketed under trade names REGALIA® and MILSANA®) can be used in combination with other growth promoting agents such as synthetic or organic fertilizers (e.g., di-ammonium phosphate in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and, growth promoting microbes, such as *Bacillus* spp., *Pseudomonads, Rhizobia, Trichoderma*.

Seed Coating Agent

The compositions, set forth above, may be in the form of an extract in either solid/power or liquid form (such as products marketed under trade names REGALIA® and MILSANA®) and can also be used in combination seed-coating agents. Such seed coating agents include, but are not limited to, ethylene glycol, polyethylene glycol, chitosan, carboxymethyl chitosan, peat moss, resins and waxes or chemical fungicides or bactericides with either single site, multisite or unknown mode of action.

Anti-Phytopathogenic Agents

The compositions set forth above which may be in the form of an extract (such as products marketed under trade names REGALIA® and MILSANA®) can then also be used in combination with other anti-phytopathogenic agents, such as plant extracts, biopesticides, inorganic crop protectants (such as copper), surfactants (such as rhamnolipids; Gandhi et al., 2007) or natural oils such as paraffinic oil and tea tree oil possessing pesticidal properties or chemical fungicides or bactericides with either single site, multisite or unknown mode of action. As defined herein, an "anti-phytopathogenic agent" is an agent that modulates the growth of a plant pathogen, particularly a pathogen causing soil-borne disease on a plant or alternatively prevents infection of a plant by a plant pathogen. A plant pathogen includes but is not limited to a fungus, bacteria, actinomycete or virus.

As noted above, the anti-phytopathogenic agent may be a single-site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine). In a more particular embodiment, the antifungal agent is a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole). In a most particular embodiment, the antifungal agent is myclobutanil. In yet another particular embodiment, the antifungal agent is a quinone outside inhibitor (e.g., strobilurin). The strobilurin may include but is not limited to azoxystrobin, kresoxim-methyl or trifloxystrobin. In yet another particular embodiment, the anti-fungal agent is a quinone, e.g., quinoxyfen (5,7-dichloro-4-quinolyl 4-fluorophenyl ether).

In yet a further embodiment, the fungicide is a multi-site non-inorganic, chemical fungicide selected from the group consisting of chloronitrile, quinoxaline, sulphamide, phosphonate, phosphite, dithiocarbamate, chloralkylhios, phenylpyridine-amine, cyano-acetamide oxime.

In yet a further embodiment, the anti-phytopathogenic agent may be streptomycin, tetracycline, oxytetracycline, copper, kasugamycin.

Uses

The said compositions, in particular, plant extracts or compounds set forth above, may be used to modulate or more particularly promote growth of plants, e.g. crops such as fruit (e.g., strawberry), vegetable (e.g., tomato, squash, pepper, eggplant), or grain crops (e.g., soy, wheat, rice, corn), tree, flower, ornamental plants, shrubs (e.g., cotton, roses), bulb plant (e.g, onion, garlic) or vine (e.g., grape vine) and even more particularly, promote early root establishment of said plants. The compositions may be used to modulate the germination of a seed(s) in a plant(s). Alternatively, said compositions may be used to modulate the amount of soil-borne disease infection in plants and in particular, prevent or inhibit said soil borne disease infection and/or decrease the rate and/or degree of spread of said soil borne disease infection in said plants. Again, the plants include but are not limited to (e.g., strawberry), vegetable (e.g., tomato, squash, pepper, eggplant), or grain crops (e.g., soy, wheat, rice, corn), trees, flowers, ornamental plants, shrubs (e.g., cotton, roses), bulb plants (e.g., onion, garlic) or vines (e.g., grape vine). Soil borne diseases include, but are not limited to, those caused by infection by non-*Rhizoctonia* soil borne diseases such as *Pythium, Phytophthora, Vertilicillium, Sclerotium, Colletotrichum* and *Fusarium*.

The said composition (e.g., plant extract) or formulated product can be used alone or simultaneously with the other component or components set forth above, such as growth promoting agents and/or anti-phytopathogenic agents in a tank mix or in a program (sequential application called rotation) with predetermined order and application interval during the growing season. When used in a combination with the above-mentioned products, at concentration lower than recommended in the product label, the combined efficacy of the two or more products (one of which is the said plant extract) is in a preferred embodiment, higher than each individual component's effect added together. Hence, the effect is enhanced by synergism between these two (or more) products, and the risk for the development of pesticide resistance among the plant pathogenic strains is reduced.

The composition (e.g., plant extract) may be applied by root dip at transplanting, specifically by treating a fruit or vegetable with the plant extract by dipping roots of the fruit or vegetable in a suspension of said extract (about 0.25 to about 1.5% and more particularly about 0.5% to about 1.0% volume by volume) prior to transplanting the fruit or vegetable into the soil.

Alternatively, the composition (e.g., plant extract) may be applied by drip or other irrigation system. Specifically, the plant extract may be injected into a drip irrigation system. In a particular embodiment, the extract may be applied at a rate of about 11 to about 4 quarts per acre.

In yet another embodiment, the composition may be added as an in-furrow application. Specifically, the composition may be added as an in-furrow spray at planting using nozzles 30 calibrated to deliver a total output of 2-6 gallons/acre. Nozzles are placed in the furrow opener on the planter so that the pesticide application and seed drop into the furrow are simultaneous. The mixtures set forth above and, where appropriate, a solid or liquid adjuvant are prepared in known manner. For example, the mixtures may be prepared by homogeneously mixing and/or grinding the active ingredients with extenders such as solvents, solid carriers and, where appropriate, surface-active compounds (surfactants). The compositions may also contain further ingredients such as stabilizers, viscosity regulators, binders, adjuvants as well as fertilizers or other active ingredients in order to obtain special effects.

EXAMPLES

The examples set forth below are presented to describe preferred embodiments and utilities of the invention and is not meant to limit the invention unless otherwise stated in the claims appended hereto.

Example 1: Effect of *Reynoutria sachalinensis* on Strawberry Growth

A 16 acre plot of strawberry plants are treated with a solution of *Reynoutria sachalinensis* extract (sold under the trade name of REGALIA®) at a concentration of 0.25%, 0.5% and 1.0% (v/v) alone or *Streptomyces lydicus* marketed as ACTINOVATE® (Natural Industries, Inc.) by dipping plants into the REGALIA® in a 250 gallon feed trough for approximately 3 minutes. After nine days, all plants treated with REGALIA® are very healthy and actively growing whereas ACTINOVATE® treated plantings have skips in the row where plants appear dead. REGALIA® treated plants have proliferating fibrous roots whereas the ACTINOVATE® treated plants may have three or four roots growing.

Example 2: Effect of *Reynoutria sachalinensis* on Soybean Seed Germination

Dry extract of *Reynoutria sachalinensis* is dissolved in 95% ethanol at 5% (w/v) and sonicated for 10 minutes. The solution was used to coat soybean seeds at various rates.

Seed Coating:

Soybean (*Glycine max*) seeds are surface sterilized by soaking the seed in 0.5% sodium hypochlorite for 3 minutes and rinsed three times with sterile water. The following treatments are used:
1. No coating
2. Coating agent (e.g., SEPIRET® 1171-O (Becker Underwood, Inc.) at 12 g/kg seeds)
3. Coating agent plus 2 ml 95% ethanol
4. Coating agent plus *Reynoutria sachalinensis* extract at 10 g/kg seed
5. Coating agent plus *Reynoutria sachalinensis* at 2 g/kg seed
6. Coating agent plus *Reynoutria sachalinensis* at 0.2 g/kg seed
7. Coating agent plus *Reynoutria sachalinensis* at 0.05 g/kg seed
8. Coating agent plus *Reynoutria sachalinensis* at 0.025 g/kg seed
9. Coating agent plus *Reynoutria sachalinensis* at 0.0125 g/kg seed Evaluation of Germination:

The seeds from the above-mentioned treatments are placed in 10 cm petri dishes with 10 ml of sterile water and left in darkness at room temperature (25° C.). After 5 days additional 10 ml sterile water was added to each petri dish and the seeds are left uncovered to react to light for three days. The germination and color of the seeds in different treatments are compared and documented.

Results and Conclusions:

*Reynoutria sachalinensis* coated treated seeds had longer roots and greener cotyledons. Seeds coated with at 0.025 to 2 g/kg seed showed the best treatment effect.

Example 3: Effect of *Reynoutria sachalinensis* (Formulated as REGALIA®ME) on Growth of Strawberry Transplants Plant Dip:

Bare-root plants/transplants cv. Albion were used in the study. Plants were soaked in each treatment solution for 5 minutes prior to transplanting.

Treatments:
1. Untreated control (water);
2. REGALIA® ME at 0.50% v/v (1:200) used as a whole plant dip;
3. REGALIA® ME at 1.00% v/v (1:100) used as a whole plant dip;
4. REGALIA® ME at 1:200+Aliette WDG at 2.5 lb/100 gallon (3.0 g/L) used as a whole plant dip; Plants were soaked for 15 minutes following the product label;
5. ALIETTE® WDG (Bayer CropScience, contains Aluminum tris (O-ethyl phosphonate as active ingredient) 2.5 g/100 gal; Plants were soaked for 15 minutes following the product label.

There were 5 plants per replicate and there were four replicates per treatment. The treatments were arranged in a randomized complete block design.

Evaluation:

All of the plants were assessed for the percentage of white root relative to the whole root area and for the percentage of feeder roots in relation to the whole root mass volume after 14 days of treatment (Table 1).

Results and Conclusions:

There was a 42% increase in new white root area at 1:200 (v/v) and a 123% increase at 1:100 (v/v) compared to the water control. The feeder root mass also increased 14.9% at 1:200 dilution and 43% increase at 1:100 dilution (Table 1).

TABLE 1

Percentage area of white root growth and feeder roots after treated with REGALIA ® (*Data with the same letter in a column are not significantly different at LSD P = 0.05 level.)

| Treatment | White root (% area) | Feeder root (% mass vol) |
|---|---|---|
| Water | 14.7a* | 11.4a |
| REGALIA ® ME 1:200 (v/v) | 21.0a | 13.1a |
| REGALIA ® ME 1:100 (v/v) | 32.8a | 16.3a |
| REGALIA ® ME 1:200 + ALIETTE ® | 30.8a | 16.3a |
| ALIETTE ® 2.5 g/100 gal | 24.0a | 14.3a |

Example 4: Applications of *Reynoutria sachalinensis* (Formulated as REGALIA® ME) to Enhance Plant Establishment of Strawberry Plant Dip:

This study consisted of 7 treatments applied on Day 0 and Day 14 to evaluate the efficacy of REGALIA®ME for control of soil-borne diseases and enhance plant establishment and development of strawberry along the Central California Coast. The trial was conducted at Guadalupe, Calif., USA. Strawberry bare-root plants cv. Albion were planted in 3.33-ft×15-ft raised beds. The following treatments were applied.

Treatments:

There were four replicates per treatment, which were arranged in a randomized complete block design.
1. Untreated check;
2. REGALIA® ME @ 0.25% (v/v) used as a whole plant dip prior to transplanting;
3. REGALIA® ME @ 0.5% (v/v) used as a whole plant dip prior to transplanting;
4. REGALIA® ME @ 0.1% (v/v) used as a whole plant dip prior to transplanting;
5. REGALIA® ME @ 2 qt/acre applied through drip irrigation immediately after planting and two weeks hence;
6. REGALIA® ME @ 4 qt/acre applied through drip irrigation immediately after planting and two weeks hence;
7. ALIETTE WDG @ 2.5 lb/acre applied through drip irrigation immediately after planting and two weeks hence.

Evaluation:

Evaluations consisted of assessing five plants per plot for stand counts, and plant measurements on Day 7, Day 11, Day 15, Day 20, Day 25, and Day 30.

Results and Conclusions:

There was a significant increase in plant weight after dipped in or drip with REGALIA®ME (Table 2) than the untreated control. The increase in plant weight ranged from 39.6% to 71.7%.

TABLE 2

Average total strawberry plant weight (g) per replicate plot, listed by evaluation date per treatment (*Data with the same letter in a column are not significantly different at LSD P = 0.05 level.).

| Trt# | Treatment | Rate | Day 7 | Day 11 | Day 15 | Day 20 | Day 25 | Day 30 |
|---|---|---|---|---|---|---|---|---|
| 1 | Untreated check | N/A | 16.0 a* | 19.0 ab | 15.0 a | 14.5 a | 13.5 b | 13.3 c |
| 2 | REGALIA ® ME dip | 0.25% | 14.1 a | 22.8 ab | 16.3 a | 16.5 a | 21.5 a | 18.5 b |
| 3 | REGALIA ® ME dip | 0.5% | 15.0 a | 11.8 c | 16.3 a | 13.1 a | 24.3 a | 19.3 ab |
| 4 | REGALIA ® ME dip | 1.0% | 15.0 a | 10.5 c | 17.8 a | 17.5 a | 22.0 a | 22.8 a |
| 5 | REGALIA ® ME drip | 2 qt/a | 15.3 a | 13.8 bc | 17.0 a | 15.5 a | 21.8 a | 22.0 ab |
| 6 | REGALIA ® ME drip | 4 qt/a | 14.3 a | 14.3 bc | 18.3 a | 16.0 a | 21.0 a | 22.8 a |

The root weight in REGALIA®ME treated plants were also significantly increased from 52.8% to 88.9% (Table 3).

TABLE 3

Average root weight (g) of strawberry roots per replicate plot, listed by evaluation date per treatment (*Data with the same letter in a column are not significantly different at LSD P = 0.05 level.).

| Trt# | Treatment | Rate | Day 7 | Day 11 | Day 15 | Day 20 | Day 25 | Day 30 |
|---|---|---|---|---|---|---|---|---|
| 1 | Untreated check | N/A | 12.0 a* | 13.5 a | 10.0 a | 10.8 a | 9.3 b | 9.0 c |
| 2 | REGALIA ® ME dip | 0.25% | 11.1 a | 16.5 a | 11.0 a | 12.0 a | 17.0 a | 13.8 b |
| 3 | REGALIA ® ME dip | 0.5% | 11.5 a | 7.3 b | 10.5 a | 9.9 a | 19.8 a | 15.0 ab |
| 4 | REGALIA ® ME dip | 1.0% | 12.5 a | 7.5 b | 11.8 a | 13.0 a | 18.3 a | 17.0 a |
| 5 | REGALIA ® ME drip | 2 qt/a | 11.5 a | 8.8 b | 11.0 a | 11.8 a | 16.8 a | 16.3 ab |
| 6 | REGALIA ® ME drip | 4 qt/a | 10.5 a | 9.3 b | 11.8 a | 10.8 a | 17.3 a | 16.3 ab |
| 7 | ALIETTE ® ME dip | 2.5 lb/a | 10.5 a | 8.8 b | 14.3 a | 7.5 a | 16.5 a | 16.3 ab |

Example 5: Application of *Reynoutria sachalinensis* (Formulated as Regalia® ME) to Enhance Plant Growth and Yield of Strawberry Plant Dip:

The trial was conducted at Dover, Fla., USA. Bare-root strawberry plants cv. Festival were planted in double row beds with 30 plants per plot at 4-ft row spacing and 14-in plant spacing. This study consisted of 7 treatments with treatments 2, 3, 4, and 7 getting a pre-plant dip application on Day 0 and treatments 5 and 6 getting a soil drench additional one day after planting (Day 1) and drip injection applications on Day 14, Day 27 and Day 47, Day 59, and Day 78.

Treatments:
1. Untreated Check;
2. REGALIA® ME @ 0.25% (v/v) pre-planting dip;
3. REGALIA® ME @ 0.5% (v/v) pre-planting dip;
4. REGALIA® ME @ 1.0% (v/v) pre-planting dip;
5. REGALIA® ME @ 2.0 qt/a soil drench (drip);
6. REGALIA®ME @ 4.0 qt/a soil drench (drip);
7. ALIETTE®ME @ 2.5 lb/acre pre-planting dip.

There were four replicates per treatments which were arranged in randomized complete blocks. Water was added to a plastic water tanks with 25 gallons of water and Regalia was added to make the appropriate solutions for treatments 2, 3, 4, and 7. Bare-root Festival strawberry plants were dipped in the tanks and left for 10 minutes (treatments 2-4) and for 15 minutes (treatment 7).

Treatments 5 and 6 were applied through a 50 mL soil drench delivered to each plant hole with a small measuring cup at one day after planting. Subsequent applications were delivered through the drip tape via specialized small plot injection "Chem-Feed" pumps and manifolds and 0.175 acre inches of water over a period of approximately one hour.

Evaluations:

Plant vigor was rated on a scale of 0-10 (0—poor 10—excellent vigor) and recorded on Day 63. New root counts were made on Day 7, Day 14, and Day 21. After Day 21 roots were given a rating of 0-10 (0—poor 10—excellent) on Day 31 as well as Day 39 and Day 46. Total fruit yield (in grams) were taken on Day 120.

Results and Conclusion:

REGALIA® ME dripped at 4 qt/a significantly increased plant vigor (Table 4).

TABLE 4

Average plant vigor (0—poor 10—excellent) by date per treatment (*Data with the same letter in a column are not significantly different at LSD P = 0.05 level.).

| Trt# | Treatment | Rate | Day 63 |
|---|---|---|---|
| 1 | Untreated Check | N/A | 7.90 c* |
| 2 | REGALIA ® ME dip | 0.25% (v/v) | 8.15 bc |
| 3 | REGALIA ® ME dip | 0.5% (v/v) | 8.45 bc |
| 4 | REGALIA ® ME dip | 1.0% (v/v) | 8.68 b |
| 5 | REGALIA ® ME drip | 2.0 qt/a | 8.75 b |
| 6 | REGALIA ® ME drip | 4.0 qt/a | 9.40 a |
| 7 | ALIETTE ® ME dip | 2.5 lb/a | 7.78 c |

Plants treated with REGALIA® ME at other rates also increased vigor but did not reach significant level. REGALIA® ME increased or significantly increased the number of new root (Table 5). The fruit yield increased 6.9% and 9.6% after dipped at 0.5% and 0.25% REGALIA®ME, respectively (Table 6). There was also a 7.3% yield increase when dripped with REGALIA® at 4 qt/a.

TABLE 5

Average new root count by date per treatment (* Data with the same letter in a column are not significantly different at LSD P = 0.05 level.).

| Trt# | Treatment | Rate | Day 7 | Day 14 | Day 21 |
|---|---|---|---|---|---|
| 1 | Untreated Check | N/A | 8.55 a* | 14.80 cd | 23.95 c |
| 2 | REGALIA ® ME dip | 0.25% v/v | 12.40 a | 16.50 cd | 37.10 bc |
| 3 | REGALIA ® ME dip | 0.5% v/v | 9.75 a | 20.80 bcd | 46.75 abc |
| 4 | REGALIA ® ME dip | 1% v/v | 10.85 a | 29.70 ab | 50.70 ab |
| 5 | REGALIA ® ME drip | 2 qt/a | 9.65 a | 24.00 abc | 40.40 bc |
| 6 | REGALIA ® ME drip | 4 qt/a | 13.50 a | 33.50 a | 64.35 a |
| 7 | ALIETTE ® dip | 2.5 lb/a | 11.80 a | 11.90 d | 30.30 bc |

TABLE 6

Total fruit yield in grams per treatment (*Data with the same letter in a column are not significantly different at LSD P = 0.05 level.).

| Trt# | Treatment | Rate | Day 120 |
|---|---|---|---|
| 1 | Untreated Check | N/A | 4910.25 a* |
| 2 | Regalia ® ME dip | 0.25% (v/v) | 5382.25 a |
| 3 | REGALIA ® ME dip | 0.5% v/v | 5249.50 a |
| 4 | REGALIA ® ME dip | 1% v/v | 4690.50 a |
| 5 | REGALIA ® ME drip | 2 qt/a | 4386.25 a |
| 6 | REGALIA ® ME drip | 4 qt/a | 5270.25 a |
| 7 | ALIETTE ® dip | 2.5 lb/a | 5185.50 a |

Example 6: Effect of *Reynoutria sachalinensis* (Formulated as REGALIA® ME) on Growth of Tomato Transplants Plant Dip:

Transplants of processing tomato cv. Heinz 5003 were soaked in each treatment for 30 min before being planted.

Treatments:
1. Water control;
2. REGALIA®ME @ 0.5% (v/v);
3. REGALIA® ME @ 1.0% (v/v).

The treatments were arranged in randomized complete block design with four replicates per treatment. There were 12 plants per replicate.

Evaluation:

The treatments were sampled two weeks later 4 weeks later; Three plants were taken from each plot to evaluate the weight of shoots and roots.

Results and Conclusions:

Transplants treated with REGALIA®ME at 0.5% had more fresh shoot weight and significantly more root weight two and four weeks after treatment (Table 7).

TABLE 7

Average fresh shoot weight (g) and root weight (g) of tomato transplant after dipped in REGALIA ® ME (*Data with the same letter in a column are not significantly different at LSD P = 0.05 level.).

| Treatment | Average fresh shoot weight (g) (2 wk) | | Average fresh shoot weight (g) (4 wk) | |
|---|---|---|---|---|
| | Shoots | Roots | Shoots | Root |
| Water control | 3.76 a* | 1.25 c | 38.1 a | 4.2 c |
| REGALIA ®ME @ 0.5% | 5.47 a | 1.74 a | 40.3 a | 5.3 ab |
| REGALIA ®ME @ 1.0% | 3.06 a | 1.70 ab | 16.5 c | 2.3 b |

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

REFERENCES CITED

Bardin, M., J. Fargues, et al. (2008). "Compatibility between biopesticides used to control grey mold, powdery mildew and whitefly on tomato." *Biological Control* 46: 476-483.

Belanger, R. R. and M. Benyagoub (1997). "Challenges and prospects for integrated control of powdery mildews in the greenhouse." *Canadian Journal of Plant Pathology* 19: 310-314.

Bokshi, A. I., J. Jobling, et al. (2008). "A single application of Milsana followed by Bion assists in the control of powdery mildew in cucumber and helps overcome yield losses." *Journal of Horticultural Science and Biotechnology* 83: 701-706.

Daayf, F., A. Schmitt, et al. (1995). "The effects of plant extracts of *Reynoutria sachalinensis* on powdery mildew development and leaf physiology of long English cucumber." *Plant Disease* 79: 577-580.

Hafez, M. B., A. Schmitt, et al. (1999). "The side-effects of plant extracts and metabolites of *Reynoutria sachalinensis* (F. Schmidt) Nakai and conventional fungicides on the beneficial organism *Trichogramma cacoeciae* Marchal (Hym., Trichogrammatidae)." *Journal of Applied Entomology* 123: 363-368.

Konstantinidou-Doltsinis, S., E. Markellou, et al. (2007). "Control of powdery mildew of grape in Greece using Sporodex L and Milsana." *Journal of Plant Diseases and Protection* 114: 256-262.

Schmitt, A. (2002). "Induced responses by plant extracts from *Reynoutria sachalinensis*: a case study." *Bull. IOBC/WPRS* 25: 83-89.

Schmitt, A., S. Kunz, et al. (2002). *Use of Reynoutria sachalinensis plant extracts, clay preparations and Brevibacillus brevis against fungal diseases of grape berries.* Fordergemeinschaft Okologisher Obstbau e.V. (FOKO) and der Staatlichen Lehr- und Versuchsanstalt fur Wein- und Obstbau (LvWO) Weinsberg. 10th International conference on cultication technique and phytopathological problems in organic fruit-growing and viticulture; presentations at the meeting from 04-07.02.2002 Weinsberg, Germany, pp. 146-151.

Schmitt, A. and B. Seddon (2005). *Biocontrol of plant pathogens with microbial BCAs and plant extracts—advantages and disadvantages of single and combined use.* Modern fungicides and antifungal compounds IV. Proceedings of the 14th International Reinhardsbrunn Symposium 2004, BCPC, Atlon, UK, pp. 205-225.

What is claimed is:

1. A method for promoting germination of a seed of a plant comprising
   applying to said seed an amount of a composition consisting essentially of physcion and emodin derived from *Reynoutria sachalinensis*, effective to promote said germination of said seed of said plant wherein said plant is selected from soy, wheat, rice, and corn.

2. The method of claim 1, wherein the grain crop is soy.

3. The method of claim 1, wherein the composition further comprises a seed coating agent.

4. The method of claim 1, wherein the composition is applied to the seed in-furrow.

5. The method of claim 1, further comprising planting the seed.

* * * * *